United States Patent
Sinskey et al.

(10) Patent No.: US 8,314,071 B2
(45) Date of Patent: Nov. 20, 2012

(54) BIOACTIVE MOLECULES FROM CO-CULTIVATION OF MICROBES

(75) Inventors: Anthony J. Sinskey, Boston, MA (US); Philip A. Lessard, Framingham, MA (US); Kazuhiro Kurosawa, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 115 days.

(21) Appl. No.: 12/599,730

(22) PCT Filed: Dec. 22, 2008

(86) PCT No.: PCT/US2008/087936
§ 371 (c)(1),
(2), (4) Date: Mar. 16, 2010

(87) PCT Pub. No.: WO2009/117036
PCT Pub. Date: Sep. 24, 2009

(65) Prior Publication Data
US 2010/0249051 A1    Sep. 30, 2010

Related U.S. Application Data

(60) Provisional application No. 61/015,857, filed on Dec. 21, 2007.

(51) Int. Cl.
*A61K 31/70* (2006.01)
*C07H 17/02* (2006.01)

(52) U.S. Cl. .......... 514/27; 536/17.4
(58) Field of Classification Search ........... 536/16.8, 536/17.4, 17.5
See application file for complete search history.

(56) References Cited

U.S. PATENT DOCUMENTS
4,107,435 A    8/1978    Ross

FOREIGN PATENT DOCUMENTS
WO    WO 01/81358 A1    11/2001

OTHER PUBLICATIONS

Kurosawa, K. et al., "Rhodostreptomycins, antibiotics biosynthesized following horizontal gene transfer from *Streptomyces padanus* to *Rhodococcus fascians*." *J. Am. Chem. Soc.* 130(4): 1126-1127 (2008).
Kurosawa, K. et al., "Characterization of *Streptomyces* MITKK-103, a newly isolated actinomycin X2-producer." *Applied Microbiology and Biotechnology* 72(1): 145-154 (2006).
International Search Report for PCT/US08/087936 mailed Oct. 1, 2009.

*Primary Examiner* — Elli Peselev
(74) *Attorney, Agent, or Firm* — Alan W. Steele; Foley Hoag LLP

(57) ABSTRACT

Certain aspects of the invention relate to antibiotics, as well as pharmaceutically acceptable salts, pro-drugs and/or analogs thereof. Another aspect of the invention relates to methods of use of said antibiotics.

19 Claims, 2 Drawing Sheets

Figure 1

Rhodostreptomycin A (1)     Rhodostreptomycin B (2)

Figure 2

BIOACTIVE MOLECULES FROM CO-CULTIVATION OF MICROBES

RELATED APPLICATIONS

This application is the U.S. National Stage of International Patent Application No. PCT/US2008/087936, filed Dec. 22, 2008, which claims the benefit of priority to U.S. Provisional Patent Application Ser. No. 61/015,857, filed Dec. 21, 2007; both of which are hereby incorporated by reference in their entireties.

BACKGROUND

The international microbiological community continues to express serious concern that the evolution of antibiotic resistance could result in microbial strains against which currently available antibacterial agents will be ineffective. Consequently, in order to overcome the threat of widespread multi-drug resistant microorganisms, there is an on-going need to develop new antibiotics, particularly those with either a novel mechanism of action and/or containing new pharmacophore groups.

SUMMARY

One aspect of the present invention relates to compounds which demonstrate antibacterial activity, processes for their preparation, pharmaceutical compositions containing them as the active ingredient, to their use as medicaments and to their use in the manufacture of medicaments for use in the treatment of bacterial infections. For example, one aspect of the invention relates to a pure and isolated compound represented by formula I, II or III, as defined below, or a pharmaceutically acceptable salt or pro-drug thereof.

DETAILED DESCRIPTION

One aspect of the invention relates to new isomeric antibiotics produced by Rhodococcus 307CO, and consequently named Rhodostreptomycin A and B, which have been isolated and characterized by mass spectrometry and NMR spectroscopy. Surprisingly, the antibiotics biosynthesized in the *Rhodococcus* following horizontal gene transfer from the *Streptomyces* are aminoglycoside antibiotics and differ widely in the structure from actinomycins, polypeptide antibiotics that are produced by *Streptomyces*. Kurosawa, K.; Bui, V. P.; VanEssendelft, J. L.; Willis, L. B.; Lessard, P. A.; Ghiviriga, I.; Sambandan, T. G.; Rha, C. K.; Sinskey, A. J. *Appl. Microbiol. Biotechnol.* 2006, 72, 145-154.

It has become increasingly evident that horizontal gene transfer is central to microbial activities that influence our health and the environment. Nielsen, K. M.; Townsend, J. P. *Nat. Biotechnol.* 2004, 22, 1110-1114; Smets, B. F.; Barkay, T. *Nat. Rev. Microbiol.* 2005, 3, 675-678; Gogarten, J. P.; Townsend, J. P. *Nat. Rev. Microbiol.* 2005, 3, 679-687; and Thomas, C. M.; Nielsen, K. M. *Nat. Rev. Microbiol.* 2005, 3, 711-721. The influence of horizontal gene transfer in antibiotic production has not been well documented, although there is indirect evidence that it occurs. Egan, S.; Wiener, P.; Kallifidas, D.; Wellington, E. M. *Appl. Environ. Microbiol.* 1998, 64, 5061-5063; Egan, S.; Wiener, P.; Kallifidas, D.; Wellington, E. M. *Antonie van Leeuwenhoek* 2001, 79, 127-133; Ginolhac, A.; Jarrin, C.; Robe, P.; Perriere, G.; Vogel, T. M.; Simonet, P.; Nalin, R. *J. Mol. Evol.* 2005, 60, 716-725; and Williamson, N. R.; Fineran, P. C.; Leeper, F. J.; Salmond, G. P. C. *Nat. Rev. Microbiol.* 2006, 4, 887-899.

Competitive co-cultures between a multi-antibiotic resistant mutant of a strain of *Rhodococcus fascians* that does not produce an antibiotic and a strain of *Streptomyces padanus* that is a highly stable actinomycin producer were carried out. A strain (307CO) of the *Rhodococcus* emerged from one such culture with the concomitant elimination of the *Streptomyces*. Bioassays of the *Rhodococcus* showed that it produces one or more antibiotics. Genomic analysis revealed that the *Rhodococcus* 307CO harbors a large segment of DNA derived from the *Streptomyces* strain, and there was a correlation between antibiotic production and the presence of the *Streptomyces* DNA in the *Rhodococcus* 307CO. Two antibiotics were isolated, named rhodostreptomycin A (1) and B (2), from culture broths of *Rhodococcus* 307CO. These appear to be two isomers of a new class of aminoglycosides. Herein, the purification, structure elucidation, and biological activity of the rhodostreptomycins is reported.

*Rhodococcus fascians* 307CO was cultivated in a production medium consisting of 1% soluble starch, 2% glucose, 2.5% soytone, 0.4% dry yeast, 0.1% beef extract, 0.005% K2HPO4 and 0.2% NaCl, pH 7.0, at 27° C. for 5 days. Spent broth exhibited an antimicrobial activity against *S. padanus*. Using assay-guided fractionation, rhodostreptomycins A (1) and B (2) were purified by a combination of cation exchange (CM-Sephadex) and reversed-phase HPLC (Lichrospher 60RP-select B). Rhodostreptomycin A (1) and B (2) were obtained as optically active white powders; $[\alpha]^{20}_D$ −76.19 (c 0.042, $H_2O$), −40.00 (c 0.035, $H_2O$), respectively, that are highly soluble in water, but not in chloroform or n-hexane. Physicochemical properties of the compounds are quite similar. Neither isomer exhibited any appreciable UV absorption at wavelengths higher than above 200 nm.

Rhodostreptomycins A (1) and B (2) both had molecular formulas of $C_{22}H_{40}N_8O_{13}$, determined via high-resolution electrospray ionization time-of-flight mass spectrometry. Accurate mass spectra were dominated by signal corresponding to the protonated molecule at m/z) 625.2808 (theoretical m/z) 625.2788).

The hydrocarbon skeleton was revealed by NMR experiments including proton, carbon, GHMBC, DQCOSY, GHMQC, and ROESY or NOESY. The final structures with the correct position of the oxygen and nitrogen heteroatoms were elucidated using tandem ion trapping mass spectrometry. Proton and carbon (boldface) chemical shifts for rhodostreptomycins A (1) and B (2) are presented below. The two isomers differ in the configuration of the carbon atom bearing the hydroxyl group in the oxazine (C6 in Strp), which is R in rhodostreptomycin A (1) and S in rhodostreptomycin B (2). Position numbering is based on the individual numbering of the three constituent moieties, namely streptidine (Strn), R-L-streptose (Strp) and R-L-glucosamine (GlcN).

Figure 1:
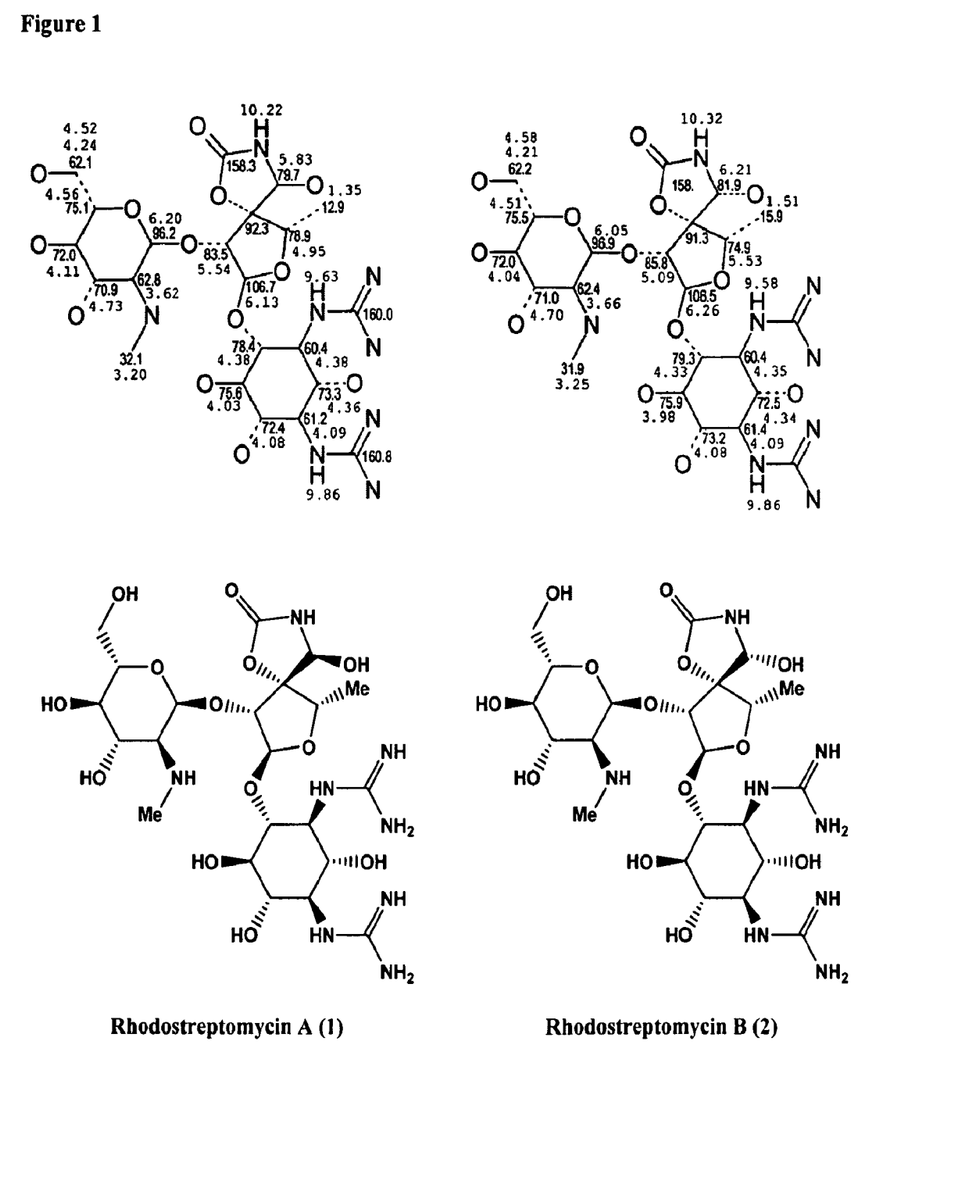
FIG. 1 depicts the structure of Rhodostreptomycin A (left column; top depiction includes NMR data) and Rhodostreptomycin B (right column; top depiction includes NMR data).
Figure 2:
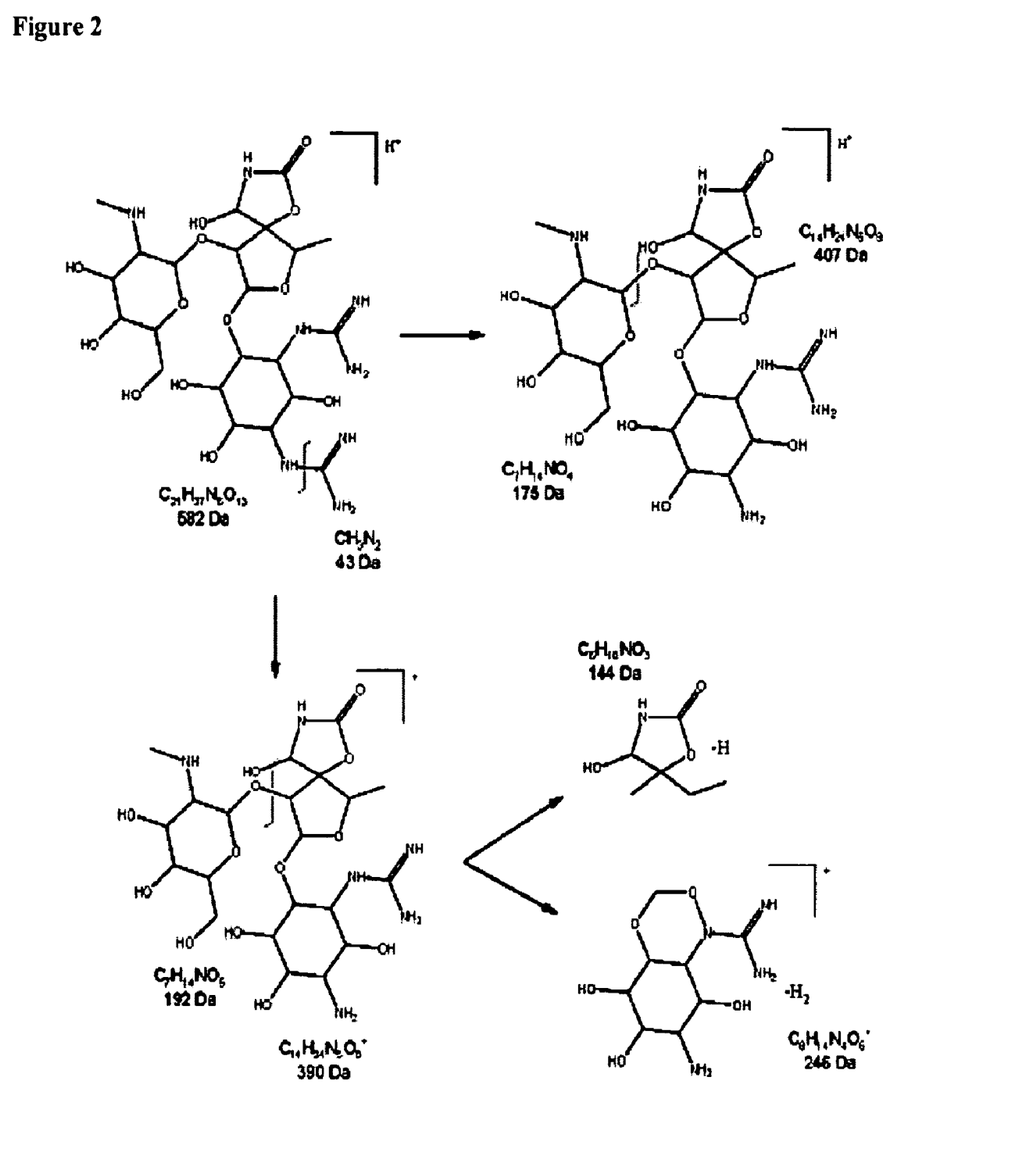
FIG. 2 depicts relevant fragments in the tandem mass spectrometric analysis of Rhodostreptomycins A and B.

Analysis of the spectra of rhodostreptomycin A (1) started with the methyl signal in the proton spectrum. Couplings in the GHMBC spectrum between the protons and the carbon of this methyl with the proton and carbon at 3.62/62.8 identified position 2 in GlcN. The sequence of the protons in the GlcN moiety was revealed by the DQCOSY spectrum. The size of the vicinal proton-proton couplings allowed for the assignment of the relative configuration of the carbons on the GlcN ring. Coupling between 6.20 and 75.1 confirmed the pyranose ring. The couplings between 6.20 and 83.5 and between 5.54 and 96.2 identified the C—H bound to the oxygen in position 1 of GlcN. 5.54 couples in the DQCOSY spectrum with 6.13, which couples with the carbons at 92.3 and 78.9. The latter carries 4.95, which couples with 1.35. Couplings of 1.35 with 78.9 and 92.3, together with the chemical shifts, identify the fragment −92.3(O, -)−78.9(4.95, 12.9)—O—. The coupling of 6.13 with 92.3 and 78.9 is possible only when 83.5 is bound to 92.3 and when 106.7 is bound to the oxygen on 78.9. The coupling of 5.54 with 79.7 places the latter on 92.3. The proton on 79.7, 5.83 couples in the DQCOSY spectrum with 10.22, which must be an amide proton, and in the GHMBC spectrum with 78.9, 92.3, and 158.3. The chemical shift of the latter suggests that it is in a urea, carbamate, or guanidine. The product ion fragment at m/z) 144 observed in the MS$^3$ mass spectrum (FIG. 2) indicates that this is a carbamate and confirms the 2-oxo-4-hydroxyoxazine moiety.

The NH vs O in the oxazine ring has to be bound to C6, as indicated by i) chemical shifts of C3 and C6 in Strp and ii) crosspeaks between 5.83 and 10.22 in the DQCOSY and ROESY spectra.

Couplings in the GHMBC spectrum between 6.13/106.7 and 4.38/78.4 identified the latter as position 4 in Strn. The guanine protons at 9.63 and 9.86 displayed couplings with the protons at 4.38 and 4.09, respectively. All of the protons on the Strn moiety show a triplet with a large coupling constant in the f2 dimension of the GHMQC spectrum, indicative of their axial positioning.

The NOEs in the ROESY spectrum were used to determine the stereochemistry of the Strp moiety. Strong NOEs of 4.95 with 5.54 and 4.38 indicate that 4.95, 5.54 and Strn are on the same side of the five-membered ring. The configuration of C6 in Strp was elucidated by NOEs between 5.83 and the protons at 4.95 and 1.35. A strong NOE between 5.83 and 4.95 established the configuration of C3 in Strp. Other NOEs reveal the conformational preferences about the glycosidic linkages and agree with the conformations found for streptomycin. Corzana, F.; Cuesta, I.; Bastida, A.; Hidalgo, A.; Latorre, M.; Gonzalez, C.; Garcia-Junceda, E.; Jimenez-Barbero, J.; Asensio, J. L. Chem. Eur. J. 2005, 11, 5102-5113. A/A' with $\Phi/\Psi_{Strp/Strn}$ 55±10/25±10 and $\Phi/\Psi_{GlcN/Strp}$ 55±10/45±10, and B/B' with $\Phi/\Psi_{Strp/Strn}$ 30±10/−50±10 and $\Phi/\Psi_{GlcN/Strp}$ 30±10/−60±10. Representative NOEs are: (i) 4.56 with 6.13 and 5.54; (ii) 3.20 with 1.35; (iii) 9.63 with 5.54; (iv) 4.03 with 5.54; (v) 6.13 with 9.63; (vi) 5.54 with 3.20; (vii) 4.03 with 6.13; (viii) 5.54 with 6.20.

Rhodostreptomycin B (2) displays the same couplings in the DQCOSY, GHMQC, and GHMBC spectra as rhodostreptomycin A (1). They also yielded the same fragmentation data, indicating identical connectivity. The strong NOE of 6.21 with 5.09 demonstrates that the two isomers have the same stereochemistry at C3 Strp and the opposite stereochemistry at C6 Strp. Inter-residue NOEs in (2) similar to those in (1), for example, 4.51 with 5.09 and 6.26, demonstrate that the two compounds exist in similar conformations in pyridine solution.

TABLE 1

Antimicrobial Activity of Rhodostreptomycins A (1) and B (2)

| organism | diameter of inhibition zone (mm) | |
|---|---|---|
| | 1 | 2 |
| Streptomyces padanus | 15 | 18 |
| Escherichia coli | 8 | 12 |
| Staphylococcus aureus | 9 | 14 |

TABLE 1-continued

Antimicrobial Activity of Rhodostreptomycins A (1) and B (2)

| organism | diameter of inhibition zone (mm) | |
|---|---|---|
| | 1 | 2 |
| Bacillus subtilis | 8 | 14 |
| Helicobacter pylori | 10 | 18 |
| Saccharomyces cerevisiae | 0 | 0 |

Rhodostreptomycins exhibited good antibiotic activities against an extensive range of Gram-negative and Gram-positive bacteria, including H. pylori in conventional disk assays run on microbial lawns (Table 1, wherein the data was collected based on a paper disk (6 mm in diameter) containing each sample (30 μg) being placed on agar plates with the organism listed.). The activity of rhodostreptomycin B (2) was more potent than that of rhodostreptomycin A (1), suggesting that the difference in stereochemistry between (1) and (2) influences the biological activity. No evidence of activity against eukaryotes, such as S. cerevisiae or cytotoxicity against human leukemia (HL-60) was observed.

Compounds of the Invention

One aspect of the invention relates to a pure and isolated compound represented by formula I or a pharmaceutically acceptable salt or pro-drug thereof:

I wherein, independently for each occurrence,

X is O or S;

Y is O, S or N($R^7$);

$R^1$ is hydrogen or an hydroxyl-protecting group, or two $R^1$ taken together are a bridging hydroxyl-protecting group;

$R^2$ is hydrogen or an amino-protecting group;

$R^3$ is hydrogen or an amino-protecting group;

$R^4$ is hydrogen or an amino-protecting group;

$R^5$ is hydrogen, an amino-protecting group, alkyl, haloalkyl, or silyl;

$R^6$ is hydrogen or an amino-protecting group;

$R^7$ is hydrogen or an amino-protecting group; and the stereochemical configuration at any undefined stereocenter is R, S, or a mixture of these configurations.

Another aspect of the invention relates to a pure and isolated compound represented by formula II or a pharmaceutically acceptable salt or pro-drug thereof:

(II)

wherein, independently for each occurrence,

X is O or S;

Y is O, S or N($R^7$);

$R^1$ is hydrogen or an hydroxyl-protecting group, or two $R^1$ taken together are a bridging hydroxyl-protecting group;

$R^2$ is hydrogen or an amino-protecting group;

$R^3$ is hydrogen or an amino-protecting group;

$R^4$ is hydrogen or an amino-protecting group;

$R^5$ is hydrogen, an amino-protecting group, alkyl, haloalkyl, or silyl;

$R^6$ is hydrogen or an amino-protecting group; and $R^7$ is hydrogen or an amino-protecting group.

Yet another aspect of the invention relates to a pure and isolated compound represented by formula III or a pharmaceutically acceptable salt or pro-drug thereof:

III wherein, independently for each occurrence,

X is O or S;

Y is O, S or N($R^7$);

$R^1$ is hydrogen or an hydroxyl-protecting group, or two $R^1$ taken together are a bridging hydroxyl-protecting group;

$R^2$ is hydrogen or an amino-protecting group;

$R^3$ is hydrogen or an amino-protecting group;

$R^4$ is hydrogen or an amino-protecting group;

$R^5$ is hydrogen, an amino-protecting group, alkyl, haloalkyl, or silyl;

$R^6$ is hydrogen or an amino-protecting group; and $R^7$ is hydrogen or an amino-protecting group.

In certain embodiments, the invention relates to any one of the aforementioned pure and isolated compounds, wherein X is O. In certain embodiments, the invention relates to any one of the aforementioned pure and isolated compounds, wherein X is S.

In certain embodiments, the invention relates to any one of the aforementioned pure and isolated compounds, wherein Y is O. In certain embodiments, the invention relates to any one of the aforementioned pure and isolated compounds, wherein Y is S. In certain embodiments, the invention relates to any one of the aforementioned pure and isolated compounds, wherein Y is N($R^7$).

In certain embodiments, the invention relates to any one of the aforementioned pure and isolated compounds, wherein $R^1$ is hydrogen, alkanoyl or silyl.

In certain embodiments, the invention relates to any one of the aforementioned pure and isolated compounds, wherein $R^1$ is hydrogen.

In certain embodiments, the invention relates to any one of the aforementioned pure and isolated compounds, wherein $R^2$ is hydrogen, alkanoyl, alkyloxycarbonyl or aralkyloxycarbonyl.

In certain embodiments, the invention relates to any one of the aforementioned pure and isolated compounds, wherein $R^2$ is hydrogen.

In certain embodiments, the invention relates to any one of the aforementioned pure and isolated compounds, wherein $R^3$ is hydrogen, alkanoyl, alkyloxycarbonyl or aralkyloxycarbonyl.

In certain embodiments, the invention relates to any one of the aforementioned pure and isolated compounds, wherein $R^3$ is hydrogen.

In certain embodiments, the invention relates to any one of the aforementioned pure and isolated compounds, wherein $R^4$ is hydrogen, alkanoyl, alkyloxycarbonyl or aralkyloxycarbonyl.

In certain embodiments, the invention relates to any one of the aforementioned pure and isolated compounds, wherein $R^4$ is hydrogen.

In certain embodiments, the invention relates to any one of the aforementioned pure and isolated compounds, wherein $R^5$ is hydrogen, alkyl, silyl, alkanoyl, alkyloxycarbonyl or aralkyloxycarbonyl.

In certain embodiments, the invention relates to any one of the aforementioned pure and isolated compounds, wherein $R^5$ is hydrogen.

In certain embodiments, the invention relates to any one of the aforementioned pure and isolated compounds, wherein $R^6$ is hydrogen, alkanoyl, alkyloxycarbonyl or aralkyloxycarbonyl.

In certain embodiments, the invention relates to any one of the aforementioned pure and isolated compounds, wherein $R^6$ is hydrogen.

In certain embodiments, the invention relates to any one of the aforementioned pure and isolated compounds, wherein $R^7$ is hydrogen, alkanoyl, alkyloxycarbonyl or aralkyloxycarbonyl.

In certain embodiments, the invention relates to any one of the aforementioned pure and isolated compounds, wherein $R^7$ is hydrogen.

One aspect of the invention relates to a pure and isolated compound selected from the group consisting of Rhodostreptomycin A and pharmaceutically acceptable salts and pro-drugs thereof.

One aspect of the invention relates to a pure and isolated compound selected from the group consisting of Rhodostreptomycin B and pharmaceutically acceptable salts and pro-drugs thereof.

One aspect of the invention relates to a Rhodostreptomycin A or B analog, or pharmaceutically acceptable salt and/or pro-drug thereof, wherein the glucosamine portion of the Rhodostreptomycin A or B is replaced with another hexose sugar.

One aspect of the invention relates to a Rhodostreptomycin A or B analog, or pharmaceutically acceptable salt and/or pro-drug thereof, wherein the glucosamine portion of the Rhodostreptomycin A or B is replaced with a sugar selected from the group consisting of fucosamine, galactosamine, glucosaminitol mannosamine, and rhamnosamine.

Methods of the Invention

One aspect of the invention relates to a method of treating a bacterial infection, comprising the step of administering to a subject in need thereof a therapeutically effective amount of a compound of formula I or a pharmaceutically acceptable salt or pro-drug thereof:

I wherein, independently for each occurrence,
X is O or S;
Y is O, S or N(R$^7$);
R$^1$ is hydrogen or an hydroxyl-protecting group, or two R$^1$ taken together are a bridging hydroxyl-protecting group;
R$^2$ is hydrogen or an amino-protecting group;
R$^3$ is hydrogen or an amino-protecting group;
R$^4$ is hydrogen or an amino-protecting group;
R$^5$ is hydrogen, an amino-protecting group, alkyl, haloalkyl, or silyl;
R$^6$ is hydrogen or an amino-protecting group;
R$^7$ is hydrogen or an amino-protecting group; and
the stereochemical configuration at any undefined stereocenter is R, S, or a mixture of these configurations.

One aspect of the invention relates to a method of treating a bacterial infection, comprising the step of administering to a subject in need thereof a therapeutically effective amount of a compound of formula II or a pharmaceutically acceptable salt or pro-drug thereof:

(II)

wherein, independently for each occurrence,
X is O or S;
Y is O, S or N(R$^7$);
R$^1$ is hydrogen or an hydroxyl-protecting group, or two R$^1$ taken together are a bridging hydroxyl-protecting group;
R$^2$ is hydrogen or an amino-protecting group;
R$^3$ is hydrogen or an amino-protecting group;
R$^4$ is hydrogen or an amino-protecting group;
R$^5$ is hydrogen, an amino-protecting group, alkyl, haloalkyl, or silyl;
R$^6$ is hydrogen or an amino-protecting group; and
R$^7$ is hydrogen or an amino-protecting group.

One aspect of the invention relates to a method of treating a bacterial infection, comprising the step of administering to a subject in need thereof a therapeutically effective amount of a compound of formula III or a pharmaceutically acceptable salt or pro-drug thereof:

III wherein, independently for each occurrence,
X is O or S;
Y is O, S or N(R$^7$);
R$^1$ is hydrogen or an hydroxyl-protecting group, or two R$^1$ taken together are a bridging hydroxyl-protecting group;
R$^2$ is hydrogen or an amino-protecting group;
R$^3$ is hydrogen or an amino-protecting group;
R$^4$ is hydrogen or an amino-protecting group;

R⁵ is hydrogen, an amino-protecting group, alkyl, haloalkyl, or silyl;

R⁶ is hydrogen or an amino-protecting group; and

R⁷ is hydrogen or an amino-protecting group.

In certain embodiments, the invention relates to any one of the aforementioned methods, wherein X is O. In certain embodiments, the invention relates to any one of the aforementioned methods, wherein X is S.

In certain embodiments, the invention relates to any one of the aforementioned methods, wherein Y is O. In certain embodiments, the invention relates to any one of the aforementioned methods, wherein Y is S. In certain embodiments, the invention relates to any one of the aforementioned methods, wherein Y is N(R⁷).

In certain embodiments, the invention relates to any one of the aforementioned methods, wherein R¹ is hydrogen, alkanoyl or silyl.

In certain embodiments, the invention relates to any one of the aforementioned methods, wherein R¹ is hydrogen.

In certain embodiments, the invention relates to any one of the aforementioned methods, wherein R² is hydrogen, alkanoyl, alkyloxycarbonyl or aralkyloxycarbonyl.

In certain embodiments, the invention relates to any one of the aforementioned methods, wherein R² is hydrogen.

In certain embodiments, the invention relates to any one of the aforementioned methods, wherein R³ is hydrogen, alkanoyl, alkyloxycarbonyl or aralkyloxycarbonyl.

In certain embodiments, the invention relates to any one of the aforementioned methods, wherein R³ is hydrogen.

In certain embodiments, the invention relates to any one of the aforementioned methods, wherein R⁴ is hydrogen, alkanoyl, alkyloxycarbonyl or aralkyloxycarbonyl.

In certain embodiments, the invention relates to any one of the aforementioned methods, wherein R⁴ is hydrogen.

In certain embodiments, the invention relates to any one of the aforementioned methods, wherein R⁵ is hydrogen, alkyl, silyl, alkanoyl, alkyloxycarbonyl or aralkyloxycarbonyl.

In certain embodiments, the invention relates to any one of the aforementioned methods, wherein R⁵ is hydrogen.

In certain embodiments, the invention relates to any one of the aforementioned methods, wherein R⁶ is hydrogen, alkanoyl, alkyloxycarbonyl or aralkyloxycarbonyl.

In certain embodiments, the invention relates to any one of the aforementioned methods, wherein R⁶ is hydrogen.

In certain embodiments, the invention relates to any one of the aforementioned methods, wherein R⁷ is hydrogen, alkanoyl, alkyloxycarbonyl or aralkyloxycarbonyl.

In certain embodiments, the invention relates to any one of the aforementioned methods, wherein R⁷ is hydrogen.

One aspect of the invention relates to a method of treating a bacterial infection, comprising the step of administering to a subject in need thereof a therapeutically effective amount of a compound selected from the group consisting of Rhodostreptomycin A and pharmaceutically acceptable salts and pro-drugs thereof.

One aspect of the invention relates to a method of treating a bacterial infection, comprising the step of administering to a subject in need thereof a therapeutically effective amount of a compound selected from the group consisting of Rhodostreptomycin B and pharmaceutically acceptable salts and pro-drugs thereof.

In certain embodiments, the invention relates to any one of the aforementioned methods, wherein the subject is infected with a Gram-negative bacterium.

In certain embodiments, the invention relates to any one of the aforementioned methods, wherein the subject is infected with a Gram-positive bacterium.

In certain embodiments, the invention relates to any one of the aforementioned methods, wherein the subject is infected with *Streptomyces padanus, Escherichia coli, Staphylococcus aureus, Bacillus subtilis, Helicobacter pylori* or *Saccharomyces cerevisiae.*

In certain embodiments, the invention relates to any one of the aforementioned methods, wherein the subject is infected with *Helicobacter pylori.*

One aspect of the invention relates to a method of treating a bacterial infection, comprising the step of administering to a subject in need thereof a therapeutically effective amount of a Rhodostreptomycin A or B analog, or pharmaceutically acceptable salt and/or pro-drug thereof, wherein the glucosamine portion of the Rhodostreptomycin A or B is replaced with another hexose sugar.

One aspect of the invention relates to a method of treating a bacterial infection, comprising the step of administering to a subject in need thereof a therapeutically effective amount of a Rhodostreptomycin A or B analog, or pharmaceutically acceptable salt and/or pro-drug thereof, wherein the glucosamine portion of the Rhodostreptomycin A or B is replaced with a sugar selected from the group consisting of fucosamine, galactosamine, glucosaminitol mannosamine, and rhamnosamine.

DEFINITIONS

In this invention, the following definitions are applicable:

A "therapeutically effective amount" is an amount of a compound of the invention or a combination of two or more such compounds, which inhibits to any medically relevant extent the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., $—C(O)_2H$ or a moiety that contains a carboxylic acid) wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$ alkyl.

Other exemplary pro-drugs release an alcohol of a compound of the invention wherein the free hydrogen of a hydroxyl substituent is replaced by $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$ alkoxycarbonyl-oxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $—P(O)(OH)_2$, $—P(O)(O(C_1-C_6)alkyl)_2$ or glycosyl (the radical resulting from detachment of the hydroxyl of the hemiacetal of a carbohydrate).

As used herein, a "carbohydrate" (or, equivalently, a "sugar") is a saccharide (including monosaccharides, oligosaccharides and polysaccharides) and/or a molecule (including oligomers or polymers) derived from one or more monosaccharides, e.g., by reduction of carbonyl groups, by oxidation of one or more terminal groups to carboxylic acids, by replacement of one or more hydroxy group(s) by a hydrogen atom, an amino group, a thiol group or similar heteroatomic groups, etc. The term "carbohydrate" also includes derivatives of these compounds. Non-limiting examples of carbohydrates include allose ("All"), altrose ("Alt"), arabinose ("Ara"), erythrose, erythrulose, fructose ("Fru"), fucosamine ("FucN"), fucose ("Fuc"), galactosamine ("GalN"), galactose ("Gal"), glucosamine ("GlcN"), glucosaminitol ("GlcN-ol"), glucose ("Glc"), glyceraldehyde, 2,3-dihydroxypropanal, glycerol ("Gro"), propane-1,2,3-triol, glycerone ("1,3-dihydroxyacetone"), 1,3-dihydroxypropanone, gulose ("Gul"), idose ("Ido"), lyxose ("Lyx"), mannosamine ("ManN"), mannose ("Man"), psicose ("Psi"), quinovose ("Qui"), quinovosamine, rhamnitol ("Rha-ol"), rhamnosamine ("RhaN"), rhamnose ("Rha"), ribose ("Rib"), ribulose ("Rul"), sialic acid ("Sia" or "Neu"), sorbose ("Sor"), tagatose ("Tag"), talose ("Tal"), tartaric acid, erythraric/threaric acid, threose, xylose ("Xyl"), or xylulose ("Xul"). In some cases, the carbohydrate may be a pentose (i.e., having 5 carbons) or a hexose (i.e., having 6 carbons); and in certain instances, the carbohydrate may be an oligosaccharide comprising pentose and/or hexose units, e.g., including those described above.

For purposes of this invention, the chemical elements are identified in accordance with the Periodic Table of the Elements, CAS version, Handbook of Chemistry and Physics, 67th Ed., 1986-87, inside cover.

The articles "a" and "an" are used herein to refer to one or to more than one (i.e., to at least one) of the grammatical object of the article. By way of example, "an element" means one element or more than one element.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "arylalkoxy" and "heteroalkoxy" as used herein, means an aryl group or heteroaryl group, as defined herein, appended to the parent molecular moiety through an alkoxy group, as defined herein. Representative examples of arylalkoxy include, but are not limited to, 2-chlorophenylmethoxy, 3-trifluoromethylethoxy, and 2,3-methylmethoxy.

The term "alkoxyalkyl" as used herein, mean an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "amino" as used herein, refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the present invention can be optionally substituted with one, two, three, four, or five substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, silyl and silyloxy.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-yl-ethyl.

The term "arylalkoxy" or "arylalkyloxy" as used herein, means an arylalkyl group, as defined herein, appended to the parent molecular moiety through an oxygen. The term "heteroarylalkoxy" as used herein, means an heteroarylalkyl group, as defined herein, appended to the parent molecular moiety through an oxygen.

The term "arylalkylthio" as used herein, means an arylalkyl group, as defined herein, appended to the parent molecular moiety through an sulfur. The term "heteroarylalkylthio" as used herein, means an heteroarylalkyl group, as defined herein, appended to the parent molecular moiety through an sulfur.

The term "arylalkenyl" as used herein, means an aryl group, as defined herein, appended to the parent molecular moiety through an alkenyl group. A representative example is phenylethylenyl.

The term "arylalkynyl" as used herein, means an aryl group, as defined herein, appended to the parent molecular moiety through an alkynyl group. A representative example is phenylethynyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein, means an arylcarbonyl group, as defined herein, bound to the parent molecule through an alkyl group, as defined herein.

The term "arylcarbonylalkoxy" as used herein, means an arylcarbonylalkyl group, as defined herein, bound to the parent molecule through an oxygen.

The term "aryloxy" as used herein, means an aryl group, as defined herein, appended to the parent molecular moiety through an oxygen. The term "heteroaryloxy" as used herein, means a heteroaryl group, as defined herein, appended to the parent molecular moiety through an oxygen.

The term "carbonyl" as used herein, means a —C(=O)— group.

The term "carboxy" as used herein, means a —$CO_2H$ group, the anion or a salt thereof.

The term "cycloalkyl" as used herein, means monocyclic or multicyclic (e.g., bicyclic, tricyclic, etc.) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein, means a cycloalkyl group, as defined herein, appended to the parent molecular moiety through an oxygen.

The term "cyano" as used herein, means a —CN group.

The term "formyl" as used herein, means a —C(=O)H group.

The term "halo" or "halogen" means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, or 3 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, silyl and silyloxy.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, or 3 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, silyl and silyloxy.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The terms "hydroxy" and "hydroxyl" as used herein, mean an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "silyl" as used herein includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The protection of functional groups by such protecting groups, suitable reagents for their introduction, suitable protecting groups and reactions for their removal will be familiar to the person skilled in the art. Examples of suitable protecting groups can be found in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974.

Suitable hydroxyl-protecting groups may be selected, for example, from those of the acyl or ester type, e.g., lower alkanoyl, such as formyl, acetyl or isobutyroyl, benzoylformyl, chloroacetyl, dichloroacetyl, trichloroacetyl, trifluoroacetyl, methoxyacetyl, phenoxyacetyl, phenylacetyl, p-phenylacetyl, diphenylacetyl, 2,6-dichloro-4-methylphenoxyacetyl, 2,6-dichloro-4-(1,1,3,3-tetramethylbutyl)phenoxyacetyl, 2,4-bis(1,1-dimethylpropyl)phenoxyacetyl, chlorodiphenylacetyl, 3-phenylpropionyl, 4-azidobutyroyl, 4-methylthiomethoxybutyroyl, (E)-2-methyl-2-butenoyl, 4-nitro-4-methylpentanoyl, 4-pentenoyl, 4-oxopentanoyl, 4,4-(ethylenedithio)pentanoyl, 5-[3-bis(4-methoxyphenyl) hydroxymethylphenoxy)laevulinyl, pivaloyl, crotonoyl, monosuccinoyl, benzoyl, p-phenylbenzoyl, 2,4,6-trimethylbenzoyl, 2-(methylthiomethoxymethyl)benzoyl, 2-(chloroacetoxymethyl)benzoyl, 2-[(2-chloroacetoxy)ethyl]benzoyl, 2-[(2-benzyloxy)ethyl], 2-[2-(4-methoxybenzyloxy) ethyl]benzoyl, 2-iodobenzoyl, o-(dibromomethyl)benzoyl, o-(methoxycarbonyl)benzoyl, 2-chlorobenzoyl, 4-bromobenzoyl, 4-nitrobenzoyl, alkoxycarbonyl, such as methoxycarbonyl, ethoxycarbonyl, isobutoxycarbonyl, methoxymethylcarbonyl, 9-fluorenylmethoxycarbonyl, 2,2,2-trichloroethoxycarbonyl, 1,1-dimethyl-2,2,2-trichloroethoxycarbonyl, 2-(trimethylsilyl)ethoxycarbonyl, 2-(phenylsulfonyl)ethoxycarbonyl, 2-(triphenylphosphonio)ethoxycarbonyl, vinyloxycarbonyl, allyloxycarbonyl, p-nitrophenoxycarbonyl, benzyloxycarbonyl, p-methoxybenzyloxycarbonyl, 3,4-dimethoxybenzyloxycarbonyl, o-nitrobenzyloxycarbonyl, p-nitrobenzyloxycarbonyl, dansylethoxycarbonyl, 2-(4-nitrophenyl)ethoxycarbonyl, 2-(2,4-dinitrophenyl)ethoxycarbonyl, 2-cyano-1-phenylethoxycarbonyl, S-benzylthiocarbonyl, 4-ethoxy-1-naphthyloxycarbonyl, 3',5'-dimethoxybenzoinyloxycarbonyl, 2-methylthiomethoxyethoxycarbonyl, N-phenylcarbamoyl, dimethylethylphosphinothiolyl, methyldithiocarbonyl; N,N,N',N'-tetramethylphosphorodiamidoyl, sulfonyl, methanesulfonyl, benzenesulfonyl, toluenesulfonyl, 2-[(4-nitrophenyl)ethyl]sulfonyl, allylsulfonyl, 2-formylbenzenesulfonyl, nitroxy, or protecting groups of the ether type, such as methyl, substituted methyl, preferably lower alkoxymethyl, especially methoxymethyl (MOM), methylthiomethyl, (phenyldimethylsilyl)methoxymethyl, benzyloxymethyl, p-methoxybenzyloxymethyl, p-nitrobenzyloxymethyl, guaiacolmethyl, tert-butoxymethyl, 4-pentenyloxymethyl, silyloxymethyl, lower alkoxy-lower alkoxymethyl, especially 2-methoxyethoxymethyl (MEM), 2,2,2-trichloroethoxymethyl, 2-(trimethylsilyl)-ethoxymethyl or methoxymethyl, tetrahydropyranyl, 3-bromotetrahydropyranyl, tetrahydrothiopyranyl, 4-methoxythiopyranyl, 1-methoxycyclohexyl, 4-methoxytetrahydrothiopyranyl, S,S-dioxy-4-methoxytetrahydrothiopyranyl, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl; substituted ethyl, such as 1-ethoxyethyl, 1-(2-chloroethoxy)ethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tert-butyl; allyl or propargyl, substituted phenyl ethers, such as p-chlorophenyl, p-methoxyphenyl, p-nitrophenyl, 2,4-dinitrophenyl or 2,3,5,6-tetrafluoro-4-(trifluoromethyl)phenyl, benzyl, substituted benzyl, such as p-methoxybenzyl, 3,4-dimethoxybenzyl, o-nitrobenzyl, p-nitrobenzyl, p-halobenzyl, e.g., p-bromobenzyl, 2,6-dichlorobenzyl, p-cyanobenzyl, p-phenylbenzyl, 2,6-difluorobenzyl, p-azidobenzyl, 4-azido-3-chlorobenzyl, 2-trifluoromethylbenzyl or p-(methylsulfinyl)benzyl, 2- or 4-picolyl, 3-methyl-2-picolyl, 2-quinolinylmethyl, 1-pyrenylmethyl, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4''-tris(4,5-dichlorophthalimidophenyl)methyl), 4,4',4''-tris(levulinoyloxyphenyl)methyl, 4,4',4''-tris(benzoyloxyphenyl)methyl, 4,4'-dimethoxy-3''-[N-(imidazolyl-methyl)]trityl, 4,4'-dimethoxy-3''-[N-(imidazolylethyl)carbamoyl]trityl, 1,1-bis(4-methoxyphenyl)-1'-pyrenylmethyl, 4-(17-tetrahydrobenzo[a,c,g,i]fluorenylmethyl)-4',4''-dimethoxytrityl, 9-anthryl, 9-(9-phenyl)xanthenyl, 9-(9-phenyl-10-oxo)anthryl, 1,3-benzodithiolane-2-yl, S,S-dioxobenzoisothiazolyl; of the silyl ether type, such as tri-lower alkylsilyl, e.g., trimethylsilyl, triethylsilyl, triisopropylsilyl, dimethylisopropylsilyl, diethylisopropylsilyl, dimethylthexylsilyl, tert-butyldimethylsilyl or di-tert-butylmethylsilyl, tert-butyldiphenylsilyl, triphenylsilyl, diphenylmethylsilyl, tris(trimethylsilyl)silyl, (2-hydroxystyryl)dimethylsilyl, (2-hydroxystyryl)diisopropylsilyl, tert-butylmethoxyphenylsilyl or tert-butoxydiphenylsilyl.

Bridging protecting groups can likewise be used where a molecule contains two hydroxy groups (for example bridging hydroxyl-protecting groups formed by two $R^1$). In certain embodiments, a bridging hydroxy-protecting group is selected from methylene, ethylidene, tert-butylmethylidene, 1-tert-butylethylidene, 1-phenylethylidene, 1-(4-methoxyphenyl)ethylidene, 2,2,2-trichloroethylidene, vinylmethylidene, cyclopentylidene, cyclohexylidene, cycloheptylidene, benzylidene, p-methoxybenzylidene, 2,4-dimethoxybenzylidene, 3,4-dimethoxybenzylidene, 2-nitrobenzylidene, 4-nitrobenzylidene, mesitylene, phenyl-(1,2-bis(methylenyl)), methoxymethylene, ethoxymethylene, dialkylsilylene, such as tert-butylsilylene, 1,3-(1,1,3,3-tetraisopropyldisiloxanylidene), 1,1,3,3-tetra-tert-butoxydisiloxanylidene, —C(=O)—, ethylboronyl (—(CH$_3$CH$_2$)B—), phenylboronyl (-(phenyl)B—), o-acetamidophenylboronyl or especially isopropylidene.

Suitable amino-protecting groups may be selected, for example, from lower alkanoyl groups such as formyl, acetyl, propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenyl)-1-methylethoxycarbonyl, α,α-dimethyl-3,5-dimethoxybenzyloxycarbonyl, benzhydryloxycarbonyl, t-butyoxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like; and silyl groups such as trimethylsilyl and the like. Still other examples include theyl, succinyl, methoxysuccinyl, subery, adipyl, azelayl, dansyl, benzyloxycarbonyl, methoxyazelaly, methoxyadipyl, methoxysuberyl, and 2,4-dinitrophenyl.

The term 'Gram-positive bacteria' is an art recognized term for bacteria characterized by having as part of their cell wall structure peptidoglycan as well as polysaccharides and/or teichoic acids and are characterized by their blue-violet color reaction in the Gram-staining procedure. Representative Gram-positive bacteria include: *actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium* complex, *Mycobacterium chelonae, Mycobacterium fortuitum, Mycobacte-* rium haemophilium, Mycobacterium kansasii, Mycobacterium leprae, Mycobacterium marinum, Mycobacterium scrofulaceum, Mycobacterium smegmatis, Mycobacterium terse, Mycobacterium tuberculosis, Mycobacterium ulcerans, Nocardia spp., Peptococcus niger, Peptostreptococcus spp., Proprionibacterium spp., Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae (group B streptococcus), Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes (group A streptococcus), Streptococcus salivarius, and Streptococcus sanguis.

The term "Gram-negative bacteria" is an art recognized term for bacteria characterized by the presence of a double membrane surrounding each bacterial cell. Representative Gram-negative bacteria include Acinetobacter calcoaceticus, Actinobacillus actinomycetemcomitans, Aeromonas hydrophile, Alcaligenes xylosoxidans, Bacteroides, Bacteroides fragilis, Bartonella bacilliformis, Bordetella spp., Borrelia burgdorferi, Branhamella catarrhalis, Brucella spp., Campylobacter spp., Chalmydia pneumoniae, Chlamydia psittaci, Chlamydia trachomatis, Chromobacterium violaceum, Citrobacter spp., Eikenella corrodens, Enterobacter aerogenes, Escherichia coli, Flavobacterium meningosepticum, Fusobacterium spp., Haemophilus influenzae, Haemophilus spp., Helicobacter pylori, Klebsiella spp., Legionella spp., Leptospira spp., Moraxella catarrhalis, Morganella morganii, Mycoplasma pneumoniae, Neisseria gonorrhoeae, Neisseria meningitidis, Pasteurella multocida, Plesiomonas shigelloides, Prevotella spp., Proteus spp., Providencia rettgeri, Pseudomonas aeruginosa, Pseudomonas spp., Rickettsia prowazekii, Rickettsia rickettsii, Rochalimaea spp., Salmonella spp., Salmonella typhi, Serratia marcescens, Shigella spp., Treponema carateum, Treponema pallidum, Treponema pallidum endemicum, Treponema pertenue, Veillonella spp., Vibrio cholerae, Vibrio vulnificus, Yersinia enterocolitica, and Yersinia pestis.

Pharmaceutical Compositions

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a pro-drug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

Dosage

For any compound of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition). In some cases it is appropriate to determine the $IC_{50}$ in the presence of 3 to 5% serum albumin since such a determination approximates the binding effects of plasma protein on the compound. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

EXEMPLIFICATION

The invention now being generally described, it will be more readily understood by reference to the following examples which are included merely for purposes of illustration of certain aspects and embodiments of the present invention, and are not intended to limit the invention.

General Experimental Procedures

UV spectra were recorded in $H_2O$ using an Agilent Technologies 8453 spectrophotometer. Optical rotations were measured on a JASCO P-2000 polarimeter. For the mass spectrometry analysis, samples were diluted with methanol acidified to 1% with formic acid and direct infused at 10 µL/min using electrospray ionization into a ThermoFinnigan LCQ Deca ion trap mass spectrometer. The parent pseudomolecular ion [M+H]+ was trapped and fragmented via collisionally-induced dissociation using the optimal collision voltage and a 2 amu window. Observed daughter ions were trapped and fragmented sequentially with collision voltages of 25 V. Structural elucidation was performed based on daughter peak assignments. For NMR studies, samples were analyzed as pyridine-$d_5$ solutions at 25° C. The spectrometer was a Varian Inova operating at 500 MHz for H1 and 125 MHz for C13, equipped with a 5 mm indirect detection probe. Proton chemical shifts were referenced to the higher field signal of pyridine (7.22 ppm). Similarly, carbon chemical shifts were referenced to the corresponding carbon in pyridine, at 123.8 ppm. HPLC separations were performed on a model SD-200 Rainin Dynamax attached to a model UV-1 absorbance detector. All solvents used were of HPLC grade.

Producing Organism

The *Rhodococcus* strain 307CO was isolated from a coculture of a streptomycin-rifampicin-resistant derivative of *R. fascians* OD356 and *Streptomyces padanus* MITKK-103. The original strain OD356 was obtained from the DuPont Microbial Culture Collection (Wilmington, Del.), and the strain MITKK-103 was isolated in our laboratory and has been deposited as designated NRRL30828. See Kurosawa, K.; Bui, V. P.; VanEssendelft, J. L.; Willis, L. B.; Lessard, P. A.; Ghiviriga, I.; Sambandan, T. G.; Rha, C. K.; Sinskey, A. J. *Appl. Microbiol. Biotechnol.* 2006, 72, 145-54.

Production of Rhodostreptomycin A and B

The strain was stored on agar plugs in vials containing sterile 10% glycerol at −80° C. until ready for use. The culture was inoculated into a 500-mL baffled flask containing 100 mL of production medium composed of 1% soluble starch, 2% glucose, 2.5% soytone, 0.4% dry yeast, 0.1% meat extract, 0.005% $K_2HPO_4$ and 0.2% NaCl, pH 7.0. Fermentation flasks were incubated at 27° C. on a rotary shaker (250 rpm) for 5 days.

Purification of Rhodostreptomycins A and B

The culture broth of strain 307CO in 100 flasks was used as a starting material for the isolation of rhodostreptomycins. After harvesting, the culture broth was centrifuged, and the supernatant (9.5 liters) was charged on a column of CM-Sephadex C-50 (50 mL). The column was washed with deionized water and then eluted with 1 M NaCl. The antimicrobial active fractions were pooled and concentrated in vacuo. The active-fraction was dissolved in a small volume of 0.007 M sodium hexanesulfonate buffer (SHB), and repeatedly purified by a HPLC system equipped with a C18 reversed-phase column (Lichrospher 60RP-select B, 10 μm, 250×10 mm, Agilent Technologies). 0.007 M SHB was prepared by mixing 1.316 g of SHB, 0.66 mL of triethylamine, 3.96 mL of acetic acid and 60 mL of acetonitrile diluting to 1 L with water. Mobile solvent systems included 0.007 M SHB (solvent A) and acetonitrile (solvent B). The mobile phase was degassed prior to use by vacuum filtration through a 0.2 μm filter, and initially held at 100% A (5 min), linearly changed to 60% A over 25 min, held at 100% B (5 min), and equilibrated with 100% A (10 min), flowing at 3 mL/min under room temperature. The elution of each peak was collected under the monitoring at an absorbance of 254 nm by UV detector. The HPLC profile showed an antimicrobial active peak between 19 and 21 min. The antimicrobial active fractions were resubjected to a CM-Sephadex C-50 column (25 mL) to remove sodium hexanesulfonate. The CM-Sephadex column was washed with deionized water and eluted with 1 M NaCl. Fractions containing target components were concentrated by rotary evaporation. After removing the precipitate (NaCl), the aqueous solution was repeatedly purified by HPLC, using a C18 reversed-phase column (Lichrospher 60RP-select B, 250×10 mm). The chromatography was conducted at a flow rate of 3 mL min-1 using an isocratic elution of 2% acetonitrile in water containing 0.1% trifluoroacetic acid. The effluent was monitored by UV absorption at 215 nm. The antimicrobial substances A and B were fractionated at the retention time of 9.6 and 10.5 min, respectively. Each collected fraction was concentrated in vacuo, and further rechromatographed on the same HPLC column under identical elution conditions to obtain the pure substances. Finally, after freeze-drying the fractions, 28.4 mg (A) and 14.3 mg (B) of the pure rhodostreptomycins were yielded as white, hygroscopic powders.

Antimicrobial Assays

Antimicrobial activity was measured by the conventional paper disk diffusion method. See Bauer, A. W.; Kirby, W. M.; Sherris, J. C.; Turck, M. *Am. J. Clin. Pathol.* 1966, 45, 493-96; and Hachem, C. Y.; Clarridge, J. E.; Reddy, R.; Flamm, R.; Evans, D. G.; Tanaka, S. K.; Graham, D. Y. *Diagn. Microbiol. Infect. Dis.* 1996, 24, 37-41. The bioactive fractions during the purification procedures were confirmed by activity against *Streptomyces padanus*, while pure rhodostreptomycins were tested for activity against *S. padanus, Escherichia coli, Staphylococcus aureus, Bacillus subtilis, Helicobacter pylori* and *Saccharomyces cerevisiae*. In this method, each paper disk (Whatman AA Discs, 6 mm) containing the extract or 30 μg of the pure compounds was placed directly onto an agar plate that had been freshly inoculated with a lawn of the test organism. The activity was estimated by measuring the diameters of the inhibition zones.

Cytotoxicity Testing

The cytotoxicity of the compound was assessed using cultured HL-60 (human leukemia) cells as previously described. See Kurosawa, K.; Bui, V. P.; VanEssendelft, J. L.; Willis, L. B.; Lessard, P. A.; Ghiviriga, I.; Sambandan, T. G.; Rha, C. K.; Sinskey, A. J. *Appl. Microbiol. Biotechnol.* 2006, 72, 145-54.

BIOLOGICAL DEPOSIT

A biological deposit of *Rhodococcus* strain 307CO was made with Agricultural Research Service Culture Collection (NRRL), 1815 North University Street, Peoria, Ill. 61604 USA, on Mar. 8, 2012, and assigned Accession No. NRRL B-50725.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein.

We claim:

1. A pure and isolated compound represented by formula II or a pharmaceutically acceptable salt thereof:

wherein, independently for each occurrence,

X is O;

Y is O;

$R^1$ is hydrogen or an hydroxyl-protecting group, or two $R^1$ taken together are a bridging hydroxyl-protecting group;

$R^2$ is hydrogen or an amino-protecting group;

$R^3$ is hydrogen or an amino-protecting group;

$R^4$ is hydrogen or an amino-protecting group;

$R^5$ is hydrogen or an amino-protecting group; and $R^6$ is hydrogen or an amino-protecting group.

2. A pure and isolated compound represented by formula III or a pharmaceutically acceptable salt thereof:

wherein, independently for each occurrence,
X is O;
Y is O;
R¹ is hydrogen or an hydroxyl-protecting group, or two R¹ taken together are a bridging hydroxyl-protecting group;
R² is hydrogen or an amino-protecting group;
R³ is hydrogen or an amino-protecting group;
R⁴ is hydrogen or an amino-protecting group;
R⁵ is hydrogen or an amino-protecting group; and
R⁶ is hydrogen or an amino-protecting group.

3. The pure and isolated compound of claim 1 or 2, wherein R¹ is hydrogen, alkanoyl or silyl.

4. The pure and isolated compound of claim 1 or 2, wherein R¹ is hydrogen.

5. The pure and isolated compound of claim 1 or 2, wherein R² is hydrogen, alkanoyl, alkyloxycarbonyl or aralkyloxycarbonyl.

6. The pure and isolated compound of claim 1 or 2, wherein R² is hydrogen.

7. The pure and isolated compound of claim 1 or 2, wherein R³ is hydrogen, alkanoyl, alkyloxycarbonyl or aralkyloxycarbonyl.

8. The pure and isolated compound of claim 1 or 2, wherein R³ is hydrogen.

9. The pure and isolated compound of claim 1 or 2, wherein R⁴ is hydrogen, alkanoyl, alkyloxycarbonyl or aralkyloxycarbonyl.

10. The pure and isolated compound of claim 1 or 2, wherein R⁴ is hydrogen.

11. The pure and isolated compound of claim 1 or 2, wherein R⁵ is hydrogen, alkanoyl, alkyloxycarbonyl or aralkyloxycarbonyl.

12. The pure and isolated compound of claim 1 or 2, wherein R⁵ is hydrogen.

13. The pure and isolated compound of claim 1 or 2, wherein R⁶ is hydrogen, alkanoyl, alkyloxycarbonyl or aralkyloxycarbonyl.

14. The pure and isolated compound of claim 1 or 2, wherein R⁶ is hydrogen.

15. A pure and isolated compound represented by or or a pharmaceutically acceptable salt thereof.

16. A method of treating a bacterial infection, comprising the step of administering to a subject in need thereof a therapeutically effective amount of a compound of claim 1 or 2.

17. The method of claim 16, wherein the subject is infected with *Streptomyces padanus*, *Escherichia coli*, *Staphylococcus aureus*, *Bacillus subtilis*, or *Helicobacter pylori*.

18. A method of treating a bacterial infection, comprising the step of administering to a subject in need thereof a therapeutically effective amount of a compound of claim 15.

19. The method of claim 18, wherein the subject is infected with *Streptomyces padanus*, *Escherichia coli*, *Staphylococcus aureus*, *Bacillus subtilis*, or *Helicobacter pylori*.

* * * * *

UNITED STATES PATENT AND TRADEMARK OFFICE
CERTIFICATE OF CORRECTION

PATENT NO. : 8,314,071 B2
APPLICATION NO. : 12/599730
DATED : November 20, 2012
INVENTOR(S) : Anthony J. Sinskey et al.

It is certified that error appears in the above-identified patent and that said Letters Patent is hereby corrected as shown below:

On the title page item (75) Inventors: replace:

"Kazuhiro Kurosawa" with

--Kazuhiko Kurosawa--.

Signed and Sealed this
Fourth Day of June, 2013

Teresa Stanek Rea
*Acting Director of the United States Patent and Trademark Office*